United States Patent [19]

Powell et al.

[11] Patent Number: 6,140,319
[45] Date of Patent: Oct. 31, 2000

[54] VASOPEPTIDASE INHIBITORS TO TREAT ANGINA PECTORIS

[75] Inventors: James R. Powell, Washington Crossing, Pa.; Henry H. Holzgrefe, West Windsor, N.J.

[73] Assignee: Bristol-Myers Squibb Co., Princeton, N.J.

[21] Appl. No.: 09/527,120

[22] Filed: Mar. 16, 2000

Related U.S. Application Data

[60] Provisional application No. 60/126,942, Mar. 29, 1999.

[51] Int. Cl.[7] .................................................. A61K 31/55
[52] U.S. Cl. .................................. 514/211.03; 514/212.03
[58] Field of Search ........................... 514/211.03, 212.03

[56] References Cited

U.S. PATENT DOCUMENTS

| | | | |
|---|---|---|---|
| 5,030,654 | 7/1991 | Barnish et al. | 514/510 |
| 5,155,100 | 10/1992 | Erion et al. | 514/119 |
| 5,244,889 | 9/1993 | MacPherson et al. | 514/183 |
| 5,250,522 | 10/1993 | DeLombaert | 514/114 |
| 5,294,632 | 3/1994 | Erion et al. | 514/381 |
| 5,348,978 | 9/1994 | Baxter et al. | 514/547 |
| 5,354,892 | 10/1994 | Ksander | 562/444 |
| 5,508,266 | 4/1996 | Fink | 514/19 |
| 5,508,272 | 4/1996 | Robl | 514/80 |
| 5,552,397 | 9/1996 | Karanewsky et al. | 514/212 |
| 5,644,055 | 7/1997 | DeLombaert | 540/522 |
| 5,668,158 | 9/1997 | Fink | 514/354 |
| 5,744,781 | 4/1998 | Rogues et al. | 514/19 |

FOREIGN PATENT DOCUMENTS

| | | |
|---|---|---|
| 92/14706 | 9/1992 | WIPO . |
| 94/26719 | 11/1994 | WIPO . |
| 95/20571 | 8/1995 | WIPO . |
| WO 99/65500 | 12/1999 | WIPO . |

OTHER PUBLICATIONS

Yoshitomi Pharmaceutical Ind., Abstract of PCT application WO94/15908 published Jul. 21, 1994.
Cotter et al., Usefulness of Losartan, Captopril, and . . . , Am. J. Cardiol. vol. 82, p. 1024–1029 (1998).
Kloner et al., "Cardioprotection With Angiotensin Converting Enzyme . . .", Clin. Cardiol., vol. 15, p. 95–103 (1992).
Kaski et al., "Effects of Angiotensin Converting Enzyme Inhibition on Exercise Induced Angina . . .", Jour. Am. College of Cardiology, vol. 23, p. 652–657 (1994).

*Primary Examiner*—Raymond Henley, III
*Attorney, Agent, or Firm*—Stephen B. Davis

[57] ABSTRACT

Vasopeptidaes inhibitors, especially omapatrilat, are useful in treating and/or relieving the symptoms of angina pectoris. The vasopeptidase inhibitor may be used in combination with other pharmaceutically active agents.

16 Claims, 1 Drawing Sheet

VASOPEPTIDASE INHIBITORS TO TREAT ANGINA PECTORIS

This application claims priority from Ser. No. 60/126,942 filed Mar. 29, 1999.

BACKGROUND OF THE INVENTION

Over the last several years compounds have been reported in the patent and technical literature as possessing in a single molecule both angiotensin converting enzyme (ACE) inhibitory activity and neutral endopeptidase (EC24.11; NEP) inhibition activity. These compounds are of interest as cardiovascular agents particularly in the treatment of hypertension, congestive heart failure, and renal disease. These compounds are also referred to as vasopeptidase, dual metalloprotease, NEP/ACE, or ACE/NEP inhibitors.

Omapatrilat is such a vasopeptidase inhibitor which is currently undergoing clinical evaluation. Omapatrilat has the chemical name [4S-[4α(R*), 7α, 10aβ]]-octahydro-4-[(2-mercapto-1-oxo-3-phenylpropyl)amino]-5-oxo-7H-pyrido[2,1-b][1,3]thiazepine-7-carboxylic acid and the structural formula

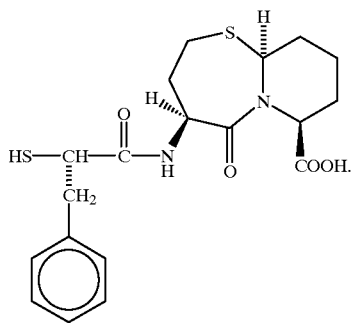

Omapatrilat, its preparation, and its use in treating cardiovascular diseases are disclosed by Robi in U.S. Pat. No. 5,508,272.

BMS 189,921 is another vasopeptidase inhibitor which is currently undergoing clinical evaluation. BMS 189,921 has the chemical name [S-(R*,R*)]-hexahydro-6-[(2-mercapto-1-oxo-3-phenylpropyl)amino]-2,2-dimethyl-7-oxo-1H-azepine-1-acetic acid and the structural formula

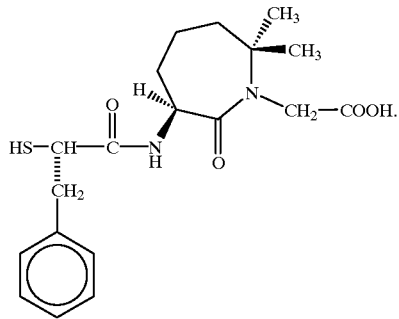

BMS 189,921, it preparation, and its use in treating cardiovascular diseases are disclosed by Karanewsky et al. in U.S. Pat. No. 5,552,397.

SUMMARY OF THE INVENTION

This invention is directed to the use of a vasopeptidase inhibitor to treat and/or relieve the symptoms of angina pectoris. Preferred vasopeptidase inhibitors for this use are omapatrilat or a pharmaceutically acceptable salt thereof, BMS 189,921 or a pharmaceutically acceptable salt thereof, or mixtures thereof. Most preferred is the use of omapatrilat.

One or more vasopeptidase inhibitors can be employed individually or in combination to treat angina pectoris according to this invention. The vasopeptidase inhibitor or inhibitors can also be employed in combination with one or more pharmaceutically active agents known to be useful in treatment of angina pectoris. Such agents include long-acting nitrates, β-adrenergic blocking agents, calcium entry blockers, antiplatelet agents, etc. The combination therapy can utilize a single dose form containing the vasopeptidase inhibitor or inhibitors or a pharmaceutically acceptable salt thereof, and the other antianginal agent or agents, co-administration of separate doses of each active agent, or administration of separate doses of each active agent according to a staggered schedule.

DETAILED DESCRIPTION OF THE INVENTION

Figure 1:
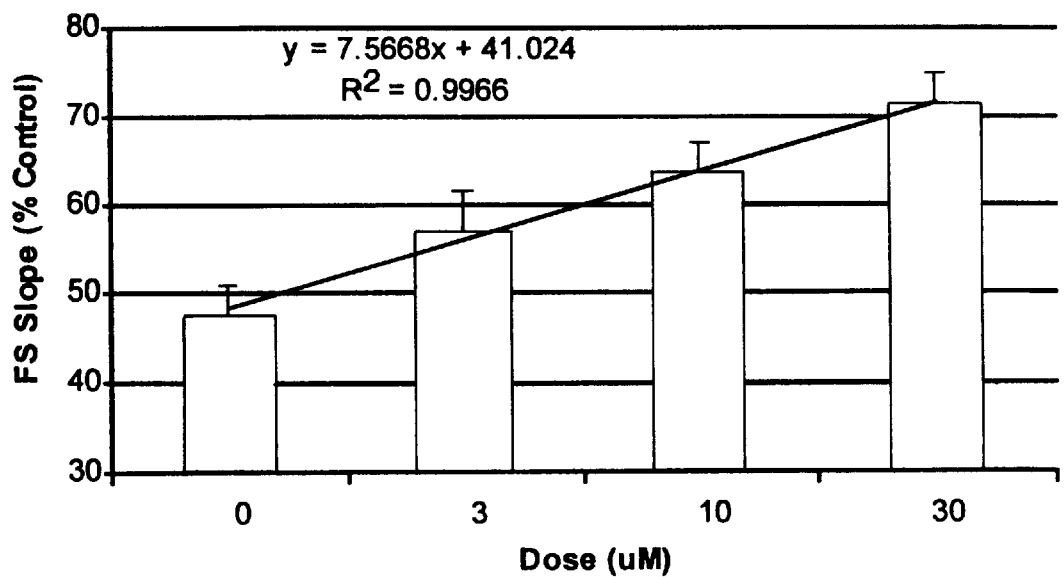
FIG. 1 is a graph showing the affect of the vasopeptidase inhibitor omapatrilat, on the Frank-Starling slope following 30 minutes of low flow ischemia in an isolated perfused rat heart model.
Figure 2:
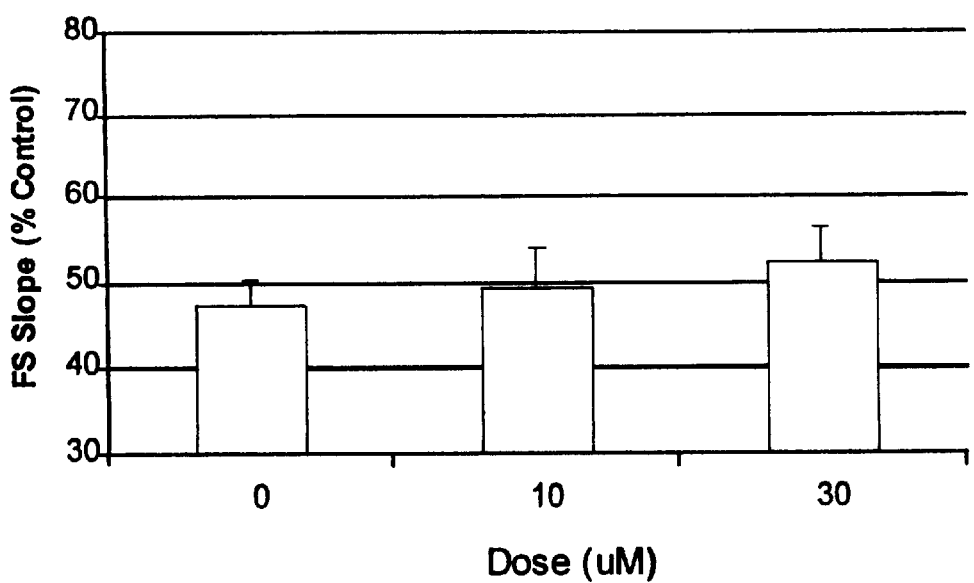
FIG. 2 is a graph showing the affect of the selective angiotensin converting enzyme inhibitor, fosinoprilat, on the Frank-Starling slope in the same isolated perfused rat heart model.

Angina pectoris is typically described as a substernal chest discomfort perceived as a tightness, heaviness, or pressure, or a burning sensation. It is characteristically nonfocal—that is, the patient does not indicate the location with one finger. The discomfort may radiate to the left shoulder or the arms, or to the neck and jaw. Some patients describe their angina in more atypical terms, such as sharp, a "gas pain", discomfort only in the jaw, teeth, forearms, or back, or discomfort beginning in the epigastric region and radiating up into the chest. Some patients describe it as shortness of breath with no definite discomfort, a sympton called angina-equivalent dyspnea.

Angina pectoris results when myocardial oxygen demand is increased to levels that cannot be met through increased coronary blood flow, usually because of stenotic atherosclerotic lesions in one or more of the epicardial coronary vessels. Accordingly, angina is typically brought on by physical exertion or emotional stress. Most patients with stable angina can identify specific activities or situations that will predictably elicit the discomfort; walking up an incline or hurrying are common examples. Some variability in the effort threshold is not uncommon. Activity done in cold weather, after meals or early in the morning may also be more likely to evoke angina. Some patients report that activity with their arms above their heads is more likely to produce the discomfort. The variable effort threshold for angina in some patients suggests that dynamic alterations in coronary blood flow (eg, because of an intermittent increase in coronary vasomotor tone) contribute to fixed atherosclerotic stenosis in limiting blood flow. Episodes of stable angina usually begin gradually and last 2 to 10 minutes. Discomfort is usually relieved promptly by rest or sublingual nitroglycerin.

Stress-induced angina also occurs in some patients with severe aortic valvular stenosis, left ventricular hypertrophy, or pulmonary arterial hypertension in the absence of significant coronary artery stenoses. In these situations, even normal coronary blood flow may be inadequate to meet the heightened myocardial oxygen demand. Angina may also develop in persons with very dilated left ventricles, particularly when accompanied by reduced diastolic coronary perfusion pressure, as in advanced aortic regurgitation.

Angina pectoris that has recently progressed or spontaneously increased in severity, frequency, or duration—particularly if accompanied by rest pain—is considered unstable angina. Patients with the recent onset of angina, particularly if it occurs at low levels of activity or at rest, are also included in this category. Most unstable angina patients have underlying obstructive coronary disease; the unpredictable onset of symptons or conversion from a stable to an unstable pattern usually results from atherosclerotic plaque fissuring with superimposed platelet—or fibrin-rich thrombi. An unstable pattern can also be precipitated by extracoronary factors (secondary unstable angina). Severe anemia or carbon monoxide exposure, for example, limits blood's capacity to carry or release oxygen and can result in angina under conditions that a patient with coronary disease might otherwise tolerate well. Uncontrolled systemic arterial hypertension, rapid dysrhythmias, or hypoxemia due to pulmonary disease can also provoke angina pectoris, as can hyperthyroidism.

Prinzmetal's angina is similar in character and location to stable angina and often responds to nitroglycerin. It characteristically occurs at rest, however, without obvious provocation or a preceding increase in heart rate or blood pressure. These features are explained by its underlying mechanism: transient coronary artery spasm. Often, the episodes occur in the early morning. Some patients with Prinzmetal's angina report other vasomotor-related symptoms such as migraine headache or Raynaud's phenomenon. See Textbook of Internal Medicine, Third Edition, pages 316–317 (1997).

This invention is directed to the use of one or more vasopeptidase inhibitors to treat and/or relieve the symptoms of angina pectoris. Preferred vasopeptidase inhibitors for this use are omapatrilat or a pharmaceutically acceptable salt thereof, and BMS 189,921 or a pharmaceutically acceptable salt thereof, particularly omapatrilat. The vasopeptidase inhibitor can be administered to a patient suffering from angina pectoris in an amount ranging from about 0.1 mg/kg to about 2.0 mg/kg per 24 hours, preferably from about 0.3 mg/kg to about 1.0 mg/kg per 24 hours. The vasopeptidase inhibitor can be administered in one or more doses over the 24 hour period to provide the total amount of active agent within the above range. If more than one dose is administered per 24 hours, the doses may be equal or may be varied in strength. Of course, the amount of active agent employed will be adjusted by the physician according to the type and severity of the angina. Also, if a combination of vasopeptidase inhibitors is employed, then one or both of the inhibitors may be administered in a lesser amount provided that the total combination of active agents administered is within the above range.

The vasopeptidase inhibitor is preferably administered orally in tablet or capsule form. However, other methods of administration may also be utilized including sublingually, bucally, parenterally such as by subcutaneous, intravenous, or intramuscular injection or infusion techniques, nasally such as by inhalation spray, topically such as in the form of a cream or ointment, transdermally as in the form of a patch that is applied to the skin, or rectally such as in the form of suppositories. The various dosage formulations contain in addition to the vasopeptidase inhibitor conventional pharmaceutically acceptable vehicles, stabilizers, preservataives, lubricants, diluents, and other conventional ingredients. The formulation may be administered for immediate release or extended release.

Another aspect of this invention is the treatment of angina pectoris with one or more vasopeptidase inhibitors, as defined above, in combination with another class of pharmaceutically active agents known to be useful in the treatment of angina pectoris. Such agents include long acting nitrates such as nitroglycerin, isosorbide mononitrate, and isosorbide dinitrate, β-adrenergic blocking agents such as propanolol hydrochloride, timolol maleate, carvedilol, metoprolol tartrate and atenolol, and calcium entry blockers such as amlodipine besylate, diltiazem hydrochloride, and verapamil hydrochloride. This invention also includes the combination of one or more vasopeptidase inhibitors and pharmaceutically active agents useful adjunctively in the treatment of angina pectoris such as antiplatelet agents. Such antiplatelat agents include clopidogrel, ticlopidine, aspirin, and dipyridamole. In such combination therapies, the amount of long acting nitrate, β-adrenegic blocking agent, calcium entry blocker, and/or antiplatelet agent employed is that previously approved for the treatment of angina or a lesser amount as determined by the treating physician. Also, in the combination therapy, the amount of vasopeptidase inhibitor may be less than the amount employed in the monotherapy described above.

The vasopeptidase inhibitor and the other pharmaceutically active agent or agents may be formulated as a single dosage form, may be co-administered from separate dosage forms, or may be administered from separate dosage forms according to a staggered schedule.

The term pharmaceutically acceptable salt includes alkali metal salts such as sodium and potassium, alkaline earth metal salts such as calcium and magnesium, salts derived from amino acids such as arginine, lysine, etc. and salts derived from amines such as alkylamines, e.g. t-butylamine, t-amylamine, etc., substituted alkylamines, e.g. benzylamine, dialkylamines, substituted dialkylamines, e.g. N-methyl glucamine, trialkylamines, substituted trialkylamines, and quaternary ammonium salts.

The following examples demonstrate the antianginal activity of the vasopeptidase inhibitor omapatrilat.

EXAMPLE 1

Isolated Perfused Rat Heart Model of Low Flow Ischemia

Methodology

Male Sprague-Dawley rats (350–450 grams) were fasted overnight and then anesthetized with sodium pentobarbital (30–40 mg/kg, ip). Following intubation by tracheotomy, the animals were ventilated with a rodent respirator (Model 683, Harvard Instruments, South Natick, Mass.) at a tidal volume of 4–5 ml delivered at 65–75 breaths/min and anticoagulated with sodium heparin (1000 IU/kg) administered via external jugular vein. A median thoracotomy was performed, the ribs were retracted, and the heart was exposed. The pericardium was removed and the ascending aorta cleared of all connective tissue. A 2–0 silk suture was placed around the base of the aorta in order to secure a perfusion cannula. The inferior vena cava was then clamped and an incision was made in the base of aorta. A custom steel cannula connected to a 3 way stopcock was quickly inserted through the incision and then secured with the preplaced suture. Retrograde extracorporeal perfusion was established with oxygenated (95% oxygen, 5% carbon dioxide, pH 7.4) Krebs-Henseleit solution comprised of (in mM) 1.25 calcium chloride, 112 sodium chloride, 25 sodium bicarbonate, 5 potassium chloride, 1 potassium biphosphate, 1.2 magnesium sulfate and 5.5 dextrose. The heart was then transferred to a standard Langendorff perfusion apparatus [Doring et al., *The isolated perfused warm-blooded heart according to Langendorff*, 1$^{st}$ ed. March: Biomesstechnik-Verlag; 1988] where it was perfused with oxygenated Krebs-Henseleit buffer warmed to 37° C. and delivered at a constant perfusion pressure of 86 mm Hg. A water fileed latex ballon was fashioned from a latex finger cot (#55613-413, VWR Scientific, S. Plainfield, N.J.) and attached to a stainless steel cannula (model LL2, Hugo Sachs, March-Hugstetten, Germany) which was then inserted into the left ventricle. The cannula was attached to a pressure transducer (model P23, Gould Instruments, Valley View, Ohio) for the measurement of developed ventricular force. The heart was then submerged in a water-jacketed (37° C.) organ bath. Perfusate flow was monitored with an extracorporeal electromagnetic flow probe (model MDL 1401, Skalar Instruments, Litchfield, Conn.). Hearts were allowed to beat at their intrinsic normal sinus rate. All data were continuously digitized at 250 Hz for subsequent analysis (Po-Neh-Mah Acquisition System, Gould Instruments, Valley View, Ohio). From the digitized data, steady state measurements for heart rate, perfusate flow and LV (left ventricular) developed pressure (LV systolic-LV end-diastolic pressure) were obtained during control, drug pretreatment, low flow and reperfusion. Hearts were prepared and assayed in quadruplicate.

Ventricular Performance

Periodic load independent indices of myocardial performance were obtained as the mean slope of the linear portion of triplicate Frank-Starling (FS) curves [Schlant, Normal physiology of the cardiovascular system. In: Hurst JW, ed. *The Heart*, 4$^{th}$ ed. New York: McGraw-Hill; 1978: 71–100]. Similarly, the mean of the peak left ventricular developed pressures (LVDP$_{max}$) obtained during each discrete series of FS curves was also recorded and meaned. FS curves were obtained by the inflation of the intraventricular balloon at a constant rate of 50 μl/min with a programmable infusion/withdrawal pump (model 44, Harvard Apparatus, South Natick, Mass.). Balloon inflation was discontinued at the onset of the descending limb of the FS curve, defined as that point where left ventricular developed pressure (LVDP) declined with further increases in balloon volume (preload). The balloon volume was then removed at 300 μl/min until LVDP was undetectable (<2 mmHg). This process was repeated until 3 reproducible curves were obtained.

Drug Preparation An Administration

The test compounds were dissolved at 2500× the delivered concentration in 100% dimethylsulfoxide (DMSO) and then infused into the distal perfusion stream of each heart with a programmable infusion pump (model 22, Harvard Apparatus, South Natick, Mass.). Each pump was controlled by a custom computer program which continuously monitored the perfusate flow in each heart, and dynamically adjusted the infusion rate of the test compound to maintain a constant DMSO concentration of 0.04%. Vehicle hearts were treated in an identical manner without drug.

Experimental Protocol

Using this model, the vasopeptidase inhibitor omapatrilat was compared to both vehicle and the selective angiotensin converting enzyme inhibitor fosinoprilat (free acid form of fosinopril). Omapatrilat was run in 20 hearts, vehicle in 21, and fosinoprilat in 19.

The maximum dose of each compound was limited to the maximum no effect hemodynamic dose, assessed in normal hearts, in order to avoid the confounding effects of pharmacologically induced cardio-depression on ventricular performance.

Following a preliminary five minute equilibration period, control FS curves were performed in each heart and LVDP$_{max}$ noted for each heart. Experimental preload (balloon volume) was then adjusted to that unique balloon volume which produced 70% of LVDP$_{max}$ in each heart. This volume was then maintained as subsequently detailed. A five minute control period ensued once the specified preload had been achieved in all hearts. At this point infusion of either drug or vehicle commenced and was continued for the remainder of the experiment.

In order to avoid confounding inotropic drug effects, the dosage rationale for drug treatment during low flow ischemia was to end with the highest concentration which did not affect steady state hemodynamics at normal perfusion pressure. Following a 5 minute control period, the drug was administered as a continuous infusion for 10 minutes at normal perfusion (86 mmHg), and throughout 45 mintues of low flow ischemia (50 mmHg). The slope of the Frank-Starling (FS) relationship was employed as a load independent index of ventricular contractile function during control and low flow ischemia. All ES data were normalized and expressed as a percent of the control FS for each heart. Data for all like groups were pooled and are expressed as mean ±sem (standard error of the mean). All groups were compared by a one way analysis of variance. A p value of <0.05 was considered significant.

| | Omapatrilat | | | |
|---|---|---|---|---|
| Dose (μM) | 0 | 3 | 10 | 30 |
| FS Slope % Control | 48.1 | 57.0 | 63.5 | 71.1 |
| sem | 2.7 | 4.2 | 3.3 | 3.9 |

| | Fosinoprilat | | |
|---|---|---|---|
| Dose (μM) | 0 | 10 | 30 |
| FS Slope % Control | 47.7 | 49.4 | 52.3 |
| sem | 2.7 | 3.4 | 3.4 |

The graphical representation of this date is shown in FIGS. 1 (omapatrilat) and 2 (fosinoprilat).

These data demonstrate that the vasopeptidase inhibitor, omapatrilat, improved the FS slope in a dose-dependent fashion ($R^2$=0.99) whereas the selective angiotensin converting enzyme inhibitor, fosinoprilat, was not significantly different from vehicle at equimolar doses.

EXAMPLE 2

Canine Model of Exertional Dysfunction

Omapatrilat (0.3 mg/kg, iv, n=7) was assessed for efficacy in a canine model of exertional myocardial dysfunction [Matsuzaki et al, "Effects of a calcium-entry blocker (diltiazem) on regional myocardial flow and function during exercise in conscious dogs" Circulation, 1984, 69, 801–814]. Instrumented dogs with collateral dependent posterior wall perfusion were trained to run on a motorized treadmill. Following a control period (Stage −2, and drug administration (Stage −1), exercise was commenced (Stage 1), and was incremented ever, two minutes until heart rate failed to increase with increasing workload, or refusal. Maximum exercise was predefined as Stage 7. Similarly, the post exercise recovery stages (8,9) were also of two minute duration. The following protocol was employed:

| Exercise stage | Speed (mph) | Kcal | Grade of treadmill (degrees) |
|---|---|---|---|
| −2 | 0 | 0.8 | 0 |
| −1 | 0 | 0.8 | 0 |
| 0 | 0 | 0.8 | 0 |
| 1 | 2.5 | 2.2 | 0 |
| 2 | 3.4 | 2.8 | 0 |
| 3 | 3.4 | 4.6 | 5 |
| 4 | 3.4 | 6.4 | 10 |
| 5 | 3.4 | 8.2 | 15 |
| 6 | 3.4 | 10.0 | 20 |
| 7 | 3.4 | 11.8 | 25 |
| 8 | 3.4 | 2.8 | 0 |
| 9 | 2.5 | 2.2 | 0 |

Systemic hemodynamics, regional myocardial wall thickening, and local ventricular electograms were continuously acquired and digitized for subsequent analysis. All exercise studies were performed in pairs, such that a vehicle treatment study was followed in 4 hours by omapatrilat. All data were normalized and expressed as a percent of the appropriate vehicle control value. All groups were compared by a one way analysis of variance or t-test for means, as appropriate. A p value of <0.05 was considered significant. The current, as well as historical and published data from similar protocols, have demonstrated that complete recovery from a single bout of acute exercise occurs within 3 hours. In the current study, complete recovery from the control exercise is confirmed by the observation that all hemodynamic values prior to the second (omapatrilat) exercise study had recovered to 100% of the respective vehicle control value.

In this experiment, omapatrilat (0.3 mg/kg, iv) did not significantly affect left ventricular systolic pressure or double product (heart rate×LV systolic pressure) during control or exercise. As each dog had a variable exercise endpoint, all exercise data were expressed as a percent of the vehicle control.

The data obtained are as follows:

| Left Ventricular Systolic (LVS) Pressure | | | | |
|---|---|---|---|---|
| Exercise stage | Vehicle | sem (standard error of the mean) | Omapatrilat | sem |
| −2 | 129.5 | 5.8 | 130.2 | 5.6 |
| −1 | 129.2 | 4.8 | 124.9 | 6.3 |
| 0 | 128.1 | 5.9 | 124.3 | 8.1 |
| 1 | 142.7 | 5.6 | 134.8 | 7.2 |
| 2 | 142.8 | 6.6 | 139.2 | 6.9 |
| 3 | 141.2 | 7.3 | 138.9 | 6.9 |
| 4 | 141.4 | 7.8 | 138.7 | 7.0 |
| 5 | 142.8 | 8.2 | 140.3 | 6.2 |

| Left Ventricular Systolic (LVS) Pressure -continued | | | | |
|---|---|---|---|---|
| Exercise stage | Vehicle | sem (standard error of the mean) | Omapatrilat | sem |
| 6 | 137.1 | 5.9 | 143.3 | 6.4 |
| 7 | 140.5 | 6.4 | 147.5 | 7.1 |
| 8 | 135.1 | 7.9 | 130.5 | 6.2 |
| 9 | 130.4 | 7.8 | 127.4 | 5.1 |

| Heart Rate | | | | |
|---|---|---|---|---|
| Exercise Stage | Vehicle | sem | Omapatrilat | sem |
| −2 | 110.2 | 8.6 | 117.3 | 8.5 |
| −1 | 106.6 | 7.0 | 127.1 | 7.8 |
| 0 | 117.7 | 10.5 | 151.5 | 12.3 |
| 1 | 168.5 | 7.3 | 182.4 | 8.1 |
| 2 | 185.2 | 5.7 | 196.2 | 7.7 |
| 3 | 192.7 | 5.4 | 203.9 | 7.1 |
| 4 | 204.2 | 4.9 | 217.1 | 6.0 |
| 5 | 221.2 | 3.4 | 230.7 | 6.5 |
| 6 | 236.1 | 5.3 | 239.4 | 6.7 |
| 7 | 247.3 | 5.9 | 245.6 | 6.0 |
| 8 | 198.3 | 4.4 | 206.2 | 8.4 |
| 9 | 174.5 | 6.0 | 182.6 | 4.9 |

| Double Product (heart rate × LV systolic pressure) | | | | |
|---|---|---|---|---|
| Exercise stage | Vehicle | sem | Omapatrilat | sem |
| −2 | 14.1 | 1.0 | 15.1 | 1.1 |
| −1 | 13.2 | 0.6 | 15.7 | 0.8 |
| 0 | 14.9 | 1.1 | 18.9 | 2.3 |
| 2 | 23.9 | 1.0 | 24.7 | 1.7 |
| 2 | 26.4 | 1.2 | 27.4 | 2.0 |
| 3 | 27.0 | 1.0 | 28.4 | 2.1 |
| 4 | 28.7 | 1.1 | 30.3 | 2.2 |
| 5 | 31.5 | 1.7 | 32.6 | 2.3 |
| 6 | 32.5 | 1.8 | 34.6 | 2.4 |
| 7 | 34.8 | 2.0 | 36.5 | 2.7 |
| 8 | 26.7 | 1.4 | 27.2 | 2.4 |
| 9 | 22.5 | 0.9 | 23.4 | 1.4 |

From the above data, it can be concluded that improvements in exercise performance can not be attributed to changes in either ventricular load or heart rate.

While systemic hemodynamics were unaffected by omapatrilat, peak exercise capacity was extended in six out of seven dogs as shown by the following data:

| Peak Exercise Capacity (Kcal) | | |
|---|---|---|
| Dog | Vehicle | Omapatrilat |
| A | 11.8 | 12.5 |
| B | 11.8 | 12.5 |
| C | 6.4 | 8.2 |
| D | 10.0 | 12.5 |

-continued

Peak Exercise Capacity (Kcal)

| Dog | Vehicle | Omapatrilat |
| --- | --- | --- |
| E | 8.2 | 12.5 |
| F | 11.8 | 11.8 |
| G | 8.2 | 10.0 |
| mean | 9.7 | 11.4 |

This increase in peak exercise capacity was accompanied by a robust increase in the ischemic area wall thickening. ($p<0.001$), and a trend toward a decrease in the ST elevation in the corresponding local 10 electrogram (P=0.06). The data collected are as shown below:

Posterior Wall Thickening

| Exercise stage | Vehicle | sem | Omapatrilat | sem |
| --- | --- | --- | --- | --- |
| −2 | 97.6 | 2.5 | 95.8 | 5.4 |
| −1 | 97.0 | 4.0 | 96.2 | 5.5 |
| 0 | 100.3 | 4.9 | 100.1 | 6.5 |
| 1 | 56.1 | 13.5 | 76.8 | 7.8 |
| 2 | 36.5 | 16.1 | 66.2 | 11.1 |
| 3 | 32.5 | 16.4 | 63.1 | 12.4 |
| 4 | 20.4 | 15.6 | 46.4 | 13.2 |
| 5 | 21.5 | 10.3 | 34.1 | 12.9 |
| 6 | 26.7 | 7.1 | 30.0 | 12.9 |
| 7 |  |  | 28.4 | 9.3 |
| 8 | 26.1 | 15.2 | 50.6 | 13.0 |
| 9 | 45.8 | 14.5 | 68.1 | 10.7 |

ST Segment

| Exercise stage | Vehicle | sem | Omapatrilat | sem |
| --- | --- | --- | --- | --- |
| −2 | 100.0 | 0.0 | 101.4 | 2.5 |
| −1 | 102.2 | 9.3 | 103.0 | 15.6 |
| 0 | 94.1 | 4.6 | 124.5 | 19.0 |
| 1 | 247.1 | 88.2 | 238.3 | 50.9 |
| 2 | 305.1 | 125.6 | 315.1 | 89.8 |
| 3 | 336.4 | 128.7 | 308.8 | 85.5 |
| 4 | 385.9 | 135.6 | 322.7 | 95.2 |
| 5 | 401.7 | 122.8 | 348.3 | 99.5 |
| 6 | 555.6 | 110.2 | 374.1 | 117.0 |
| 7 |  |  | 438.3 | 101.5 |
| 8 | 301.0 | 42.6 | 242.7 | 59.7 |
| 9 | 270.6 | 34.0 | 161.9 | 23.0 |

Posterior wall thickening was significantly improved with omapatrilat. The corresponding ST segment elevation reflected this ischemic zone function. This improvement in function is consistent with the enhanced exercise capacity shown above.

What is claimed is:

1. A method of treating and/or relieving the symptoms of angina pectoris comprising administering an effective amount of a vasopeptidase inhibitor.

2. A method of claim 1 wherein said vasopeptidase inhibitor is selected from the group consisting of omapatrilat or a pharmaceutically acceptable salt thereof, [S-(R*,R*)]-hexahydro-6-[(2-mercapto-1-oxo-3-phenylpropyl)amino]-2,2-dimethyl-7-oxo-1H-azepine-1-acetic acid or a pharmaceutically acceptable salt thereof, and mixtures thereof.

3. The method of claim 2 wherein said vasopeptidase inhibitor is omapatrilat.

4. A method of treating and/or relieving the symptoms of angina pectoris comprising administering an effective amount of a vasopeptidase inhibitor together with another pharmaceutically active agent.

5. A method of claim 4 wherein said vasopeptidase inhibitor is selected from the group consisting of omapatrilat or a pharmaceutically acceptable salt thereof, [S-(R*,R*)]-hexahydro-6-[(2-mercapto-1-oxo-3-phenylpropyl)amino]-2,2-dimethyl-7-oxo-1H-azepine-1-acetic acid or a pharmaceutically acceptable salt thereof, and mixtures thereof.

6. The method of claim 5 wherein said vasopeptidase inhibitor is omapatrilat.

7. A method of claim 4 wherein said other pharmaceutically active agent is co-administered with said vasopeptidase inhibitor.

8. A method of claim 4 wherein said other pharmaceutically active agent is administered separately from said vasopeptidase inhibitor.

9. A method of claim 4 wherein said other pharmaceutically active agent is a long acting nitrate, a β-adrenergic blocker, a calcium entry blocker, or an antiplatelet agent.

10. A method of claim 9 wherein said long acting nitrate in selected from the group consisting of nitroglycerin, isosorbide mononitrate, and isorbide dinitrate.

11. A method of claim 9 wherein said β-adrenergic agent is selected from the group consisting of propanolol hydrochloride, timolol maleate, carvedilol, metoprolol tartrate, and atenolol.

12. A method of claim 9 wherein said calcium entry blocker is selected from the group consisting of amlodipine besylate, diltiazem hydrochloride, and verapamil hydrochloride.

13. A method of claim 9 wherein said antiplatelet agent is selected from the group consisting of clopidogrel, ticlopidine, aspirin and dipyridamole.

14. A pharmaceutical composition comprising a vasopeptidase inhibitor and aspirin.

15. A pharmaceutical composition of claim 14 wherein said vasopeptidase inhibitor is selected from the group consisting of omapatrilat or a pharmaceutically acceptable salt thereof, [S-(R*,R*)]-hexahydro-6-[(2-mercapto-1-oxo-3-phenylpropyl)amino]-2,2-dimethyl-7-oxo-1H-azepine-1-acetic acid or a pharmaceutically acceptable salt thereof, and mixtures thereof.

16. The composition of claim 15 wherein said vasopeptidase inhibitor is omapatrilat and said antiplatelet agent is aspirin.

* * * * *